(12) United States Patent
Wang

(10) Patent No.: US 11,424,413 B2
(45) Date of Patent: Aug. 23, 2022

(54) ELECTROLUMINESECENT MATERIAL, METHOD FOR MANUFACTURING SAME, AND LUMINESECENT DEVICE

(71) Applicant: WUHAN CHINA STAR OPTOELECTRONICS SEMICONDUCTOR DISPLAY TECHNOLOGY CO., LTD., Hubei (CN)

(72) Inventor: Yamin Wang, Hubei (CN)

(73) Assignee: Wuhan China Star Optoelectronics Semiconductor Display Technology Co, Ltd., Hubei (CN)

( * ) Notice: Subject to any disclaimer, the term of this patent is extended or adjusted under 35 U.S.C. 154(b) by 447 days.

(21) Appl. No.: 16/607,626

(22) PCT Filed: May 14, 2019

(86) PCT No.: PCT/CN2019/086776
§ 371 (c)(1),
(2) Date: Oct. 23, 2019

(87) PCT Pub. No.: WO2020/220399
PCT Pub. Date: Nov. 5, 2020

(65) Prior Publication Data
US 2021/0408388 A1    Dec. 30, 2021

(30) Foreign Application Priority Data

Apr. 29, 2019  (CN) .......................... 201910353962.8

(51) Int. Cl.
| | | |
|---|---|---|
| *H01L 51/00* | (2006.01) | |
| *C07D 401/14* | (2006.01) | |
| *C09K 11/06* | (2006.01) | |
| *H01L 51/50* | (2006.01) | |

(52) U.S. Cl.
CPC ........ *H01L 51/0061* (2013.01); *C07D 401/14* (2013.01); *C09K 11/06* (2013.01);
(Continued)

(58) Field of Classification Search
CPC .............. H01L 51/0061; H01L 51/006; H01L 51/0072; H01L 51/5012; C07D 401/14; C09K 11/06
See application file for complete search history.

(56) References Cited

U.S. PATENT DOCUMENTS 6,800,722 B2 * 10/2004 Pei ...................... C08G 73/0633
428/917
8,545,996 B2 * 10/2013 Thompson .......... C07F 15/0033
546/10
(Continued)

FOREIGN PATENT DOCUMENTS

| CN | 101573324 A | 11/2009 |
|---|---|---|
| CN | 105503846 A | 4/2016 |
| KR | 20190007892 A | 1/2019 |

OTHER PUBLICATIONS

Minna Hou: "Highly Efficient Deep-Blue Electroluminescence from a A-π-Dπ-A Structure Based Fluoresence Material with Excition Utilizing Effciency above 25%", Applied Energy Materials, 1,7, 3243-3254; Published Jun. 19, 2018.

*Primary Examiner* — Nicholas J Tobergte

(57) ABSTRACT

The present disclosure provides an electroluminescent material, a method for manufacturing the electroluminescent material, and a luminescent device, by employing a fluorenyl group showing good planarity and strong visible π-π* absorption as π-based system, and simultaneously introducing a compound containing a carbazole group as an electron donor and a compound containing a pyridine group as an electron acceptor to realize an electroluminescent material, a method for manufacturing the electroluminescent material and a luminescent device with emitting a blue light and a high electroluminescence efficiency.

16 Claims, 3 Drawing Sheets

(52) U.S. Cl.
CPC .... *H01L 51/006* (2013.01); *C09K 2211/1007* (2013.01); *C09K 2211/1011* (2013.01); *C09K 2211/1014* (2013.01); *C09K 2211/1018* (2013.01); *H01L 51/0058* (2013.01); *H01L 51/0067* (2013.01); *H01L 51/0072* (2013.01); *H01L 51/5012* (2013.01); *H01L 51/5056* (2013.01); *H01L 51/5072* (2013.01); *H01L 51/5088* (2013.01); *H01L 51/5092* (2013.01)

(56) References Cited

U.S. PATENT DOCUMENTS

| | | | | |
|---|---|---|---|---|
| 8,557,953 | B2* | 10/2013 | Heun | H01L 51/0035 |
| | | | | 528/397 |
| 2003/0109700 | A1* | 6/2003 | Ksander | C07D 211/46 |
| | | | | 546/205 |
| 2006/0009614 | A1* | 1/2006 | Yamahara | H01B 1/122 |
| | | | | 428/411.1 |
| 2007/0187673 | A1* | 8/2007 | Zheng | H01L 51/004 |
| | | | | 313/506 |
| 2010/0133519 | A1 | 6/2010 | Chen et al. | |
| 2010/0230639 | A1* | 9/2010 | Yamada | C07C 211/54 |
| | | | | 252/500 |
| 2012/0223634 | A1* | 9/2012 | Xia | H05B 33/14 |
| | | | | 546/4 |
| 2014/0332758 | A1* | 11/2014 | Kwong | H01L 51/0072 |
| | | | | 546/77 |
| 2015/0090962 | A1* | 4/2015 | Kim | H01L 51/0072 |
| | | | | 257/40 |
| 2017/0288147 | A1 | 10/2017 | Fujita et al. | |
| 2019/0081248 | A1* | 3/2019 | Lin | H01L 51/0073 |
| 2021/0363417 | A1* | 11/2021 | Wang | H01L 51/0058 |

* cited by examiner

ELECTROLUMINESECENT MATERIAL, METHOD FOR MANUFACTURING SAME, AND LUMINESECENT DEVICE

CROSS REFERENCE TO RELATED APPLICATION

This application claims the priority of International Application No. PCT/CN2019/086776, filed on 2019 May 14, which claims priority to Chinese Application No. 201910353962.8, filed on 2019 Apr. 29. The entire disclosures of each of the above applications are incorporated herein by reference.

BACKGROUND OF INVENTION

Field of Invention

The present application relates to a display field, and particularly to an electroluminescent material, a method for manufacturing the electroluminescent material, and a luminescent device.

Description of Prior Art

In prior art, the organic light emitting diodes have characteristics of being self-luminous, and a material that mainly dominates emitted light is an electroluminescent material; however, luminous efficiency of the present electroluminescent material is low, which often leads to failure of an organic light emitting diode, therefore, it is necessary to provide an electroluminescent material, a method for manufacturing the electroluminescent material, and a luminescent device with a high luminous efficiency.

SUMMARY OF INVENTION

The present disclosure provides an electroluminescent material, a method for manufacturing the electroluminescent material, and a luminescent device.

The present disclosure provides an electroluminescent material, wherein a structural formula of the electroluminescent material is $R_3-R_2-R_1-R_2-R_3$, wherein the $R_1$ is a carbazole group, a structural formula of the $R_1$ comprises one of

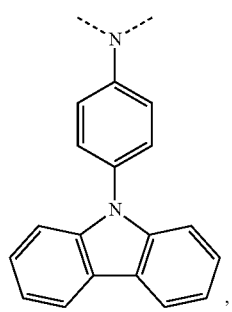

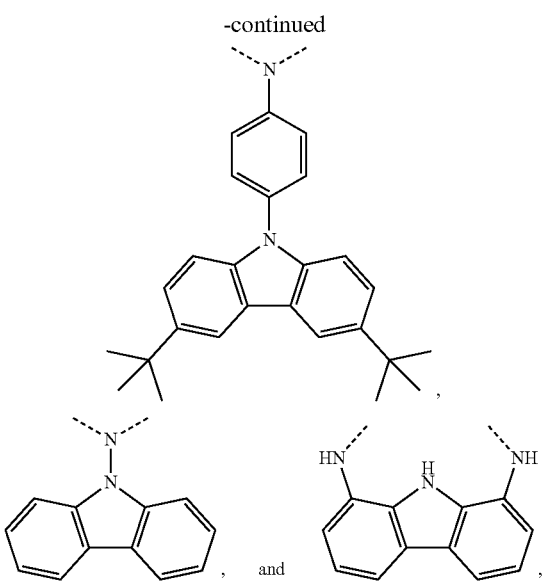

the $R_2$ is a fluorene group, a structural formula of the $R_2$ comprises one of

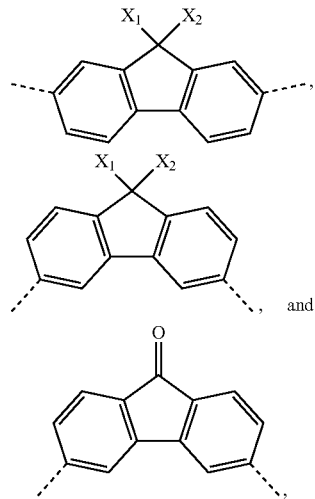

the $R_3$ is a pyridine group, a structural formula of the $R_3$ comprises one of

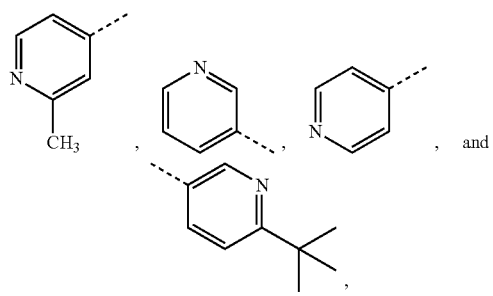

the $X_1$ comprises one of H, alkyl, alkoxy, and heteroalkyl, the $X_2$ comprises one of H, alkyl, alkoxy, and heteroalkyl.

The present disclosure also provides a method for manufacturing an electroluminescent material including:

providing a first reactant and a second reactant, and reacting the first reactant and the second reactant to generate a first intermediate product, wherein the first reactant includes a compound containing a carbazole group $R_1$, the second reactant includes a compound containing a fluorene group $R_2$, wherein a structural formula of the $R_1$ includes one of

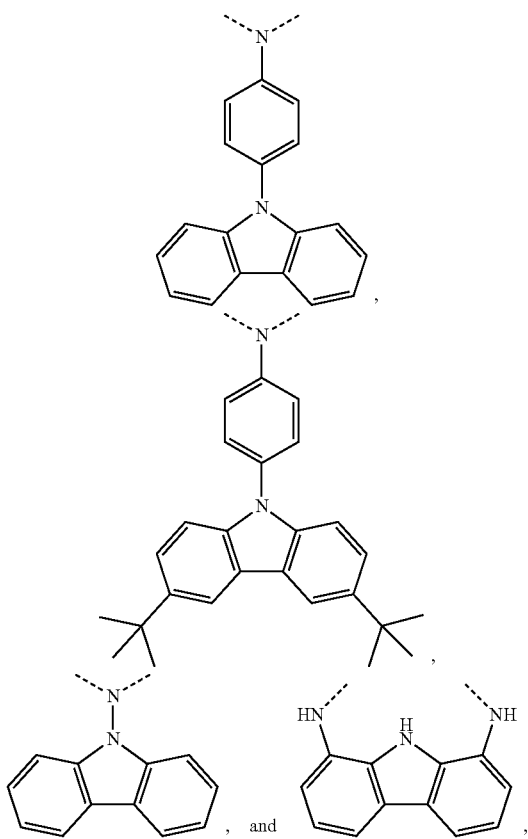

a structural formula of the $R_2$ includes one of

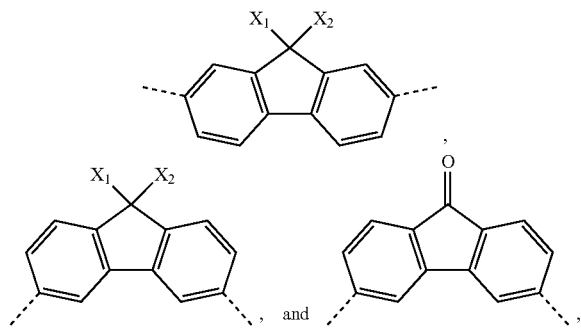

the $X_1$ includes one of H, alkyl, alkoxy, and heteroalkyl, the $X_2$ includes one of H, alkyl, alkoxy, and heteroalkyl; and providing a third reactant, and reacting the first intermediate product and the third reactant to generate the electroluminescent material, wherein a structural formula of the electroluminescent material is $R_3$—$R_2$—$R_1$—$R_2$—$R_3$, the third reactant comprises a compound containing a pyridine group $R_3$, a structural formula of the $R_3$ comprises one of

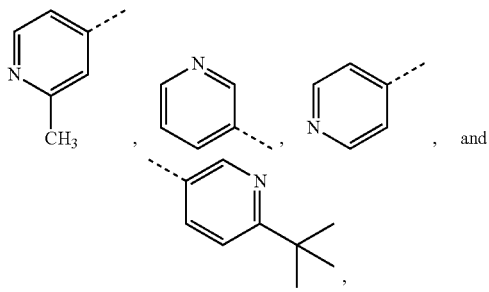

In the method for manufacturing the electroluminescent material, in the step of reacting the first reactant and the second reactant to generate a first intermediate product, a relationship between a molar weight of the first reactant and a molar weight of the second reactant is that for 1 millimole-6 millimoles of the first reactant, there are 4 millimoles-30 millimoles of the second reactant.

In the method for manufacturing the electroluminescent material, the first reactant and the second reactant are reacted in a first solvent to generate the first intermediate product, the first solvent includes one or more of toluene, tetrahydrofuran, ethanol, ethylene, perchloroethylene, trichloroethylene, acetone, ethylene glycol ether, and triethanolamine.

In the method for manufacturing the electroluminescent material, the first solvent includes a first additive, the first additive includes one or more of sodium propan-2-olate, 1,1'-bis(diphenylphosphino)ferrocene, palladium acetate, palladium chloride, [1,1'-bis(diphenylphosphino)ferrocene] palladium dichloride, tetra-triphenyl palladium, bistriphenylphosphine palladium dichloride, tris(dibenzylideneacetone)dipalladium, allyl palladium chloride (II) dimer, potassium carbonate, cesium carbonate, potassium hydroxide, sodium hydroxide, sodium t-butoxide, and sodium bicarbonate.

In the method for manufacturing the electroluminescent material, the first solvent includes toluene, the first additive includes sodium propan-2-olate, 1,1'-bis(diphenylphosphino)ferrocene, and palladium acetate.

In the method for manufacturing the electroluminescent material, a relationship among a molar weight of sodium propan-2-olate, a molar weight of 1,1'-bis(diphenylphosphino)ferrocene and a molar weight of palladium acetate in the first additive is that for 1 millimole-13 millimoles of sodium propan-2-olate, there are 0.1 millimoles-5 millimoles of 1,1'-bis(diphenylphosphino)ferrocene and 0.01 millimole-0.06 millimole of palladium acetate.

In the method for manufacturing the electroluminescent material, in the step of reacting the first intermediate product and the third reactant to generate the electroluminescent material, a relationship between a molar weight of the first intermediate product and a molar weight of the third reactant is that for 0.3 millimoles-12 millimoles of the first intermediate product, there are 0.1 millimoles-5.9 millimoles of the third reactant.

In the method for manufacturing the electroluminescent material, the first intermediate product and the third reactant are reacted in a second solvent to generate the electroluminescent material, the second solvent includes one or more of toluene, tetrahydrofuran, ethanol, ethylene, perchloroethylene, trichloroethylene, acetone, ethylene glycol ether, and triethanolamine.

In the method for manufacturing the electroluminescent material, the second solvent includes a second additive, the second additive includes one or more of tetra-triphenyl palladium, sodium propan-2-olate, 1,1'-bis(diphenylphosphino)ferrocene, palladium acetate, palladium chloride, [1,1'-bis(diphenylphosphino)ferrocene]palladium dichloride, bistriphenylphosphine palladium dichloride, tris(dibenzylideneacetone)dipalladium, allyl palladium chloride (II) dimer, potassium carbonate, cesium carbonate, potassium hydroxide, sodium hydroxide, sodium t-butoxide, and sodium bicarbonate.

In the method for manufacturing the electroluminescent material, the second solvent includes toluene, the second additive includes potassium carbonate aqueous solution, and tetrakis(triphenylphosphine)platinum.

In the method for manufacturing the electroluminescent material, in the step of providing a first reactant and a second reactant, and reacting the first reactant and the second reactant to generate a first intermediate product, wherein a reaction temperature is 90 degrees Celsius-120 degrees Celsius.

In the method for manufacturing the electroluminescent material, in the step of providing a first reactant and a second reactant, and reacting the first reactant and the second reactant to generate a first intermediate product, wherein a reaction time is 9 hours-36 hours.

In the method for manufacturing the electroluminescent material, in the step of providing a third reactant, and reacting the first intermediate product and the third reactant to generate the electroluminescent material, wherein a reaction temperature is 90 degree Celsius-120 degree Celsius.

In the method for manufacturing the electroluminescent material, in the step of providing a third reactant, and reacting the first intermediate product and the third reactant to generate the electroluminescent material, wherein a reaction time is 9 hours to 36 hours.

In the method for manufacturing the electroluminescent material, a structural formula of the first reactant includes one of

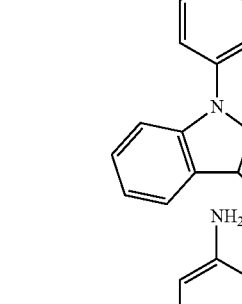

In the method for manufacturing the electroluminescent material, a structural formula of the second reactant includes one of

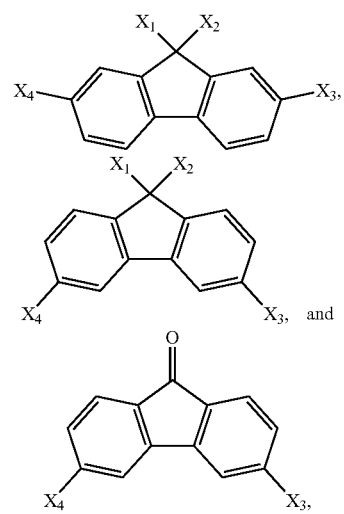

wherein the $X_3$ includes one of F, Cl, Br, and I, the $X_4$ includes one of F, Cl, Br, and I.

In the method for manufacturing the electroluminescent material, the third reactant is $R_3$—Y, the Y includes a boric acid pinacol ester group or a boric acid group.

The present disclosure also provides a luminescent device including:

a substrate layer, wherein the substrate layer includes a base and an anode layer, and the anode layer is formed on the base;

a hole injection layer, wherein the hole injection layer is formed on the anode layer;

a hole transport layer, wherein the hole transport layer is formed on the hole injection layer;

a luminescent layer, wherein the luminescent layer is formed on the hole transport layer;

an electronic transport layer, wherein the electronic transport layer is formed on the luminescent layer;

an electronic injection layer, wherein the electronic injection layer is formed on the electronic transport layer; and a cathode layer, wherein the cathode layer is formed on the electronic injection layer;

wherein the luminescent layer comprises the electroluminescent material, wherein a structural formula of the electroluminescent material is $R_3$—$R_2$—$R_1$—$R_2$—$R_3$, wherein the $R_1$ is a carbazole group, a structural formula of the $R_1$ comprises one of

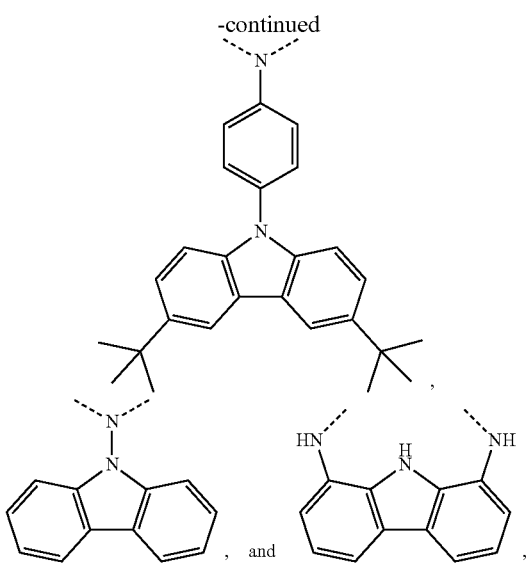

the $R_2$ is a fluorene group, a structural formula of the $R_2$ comprises one of

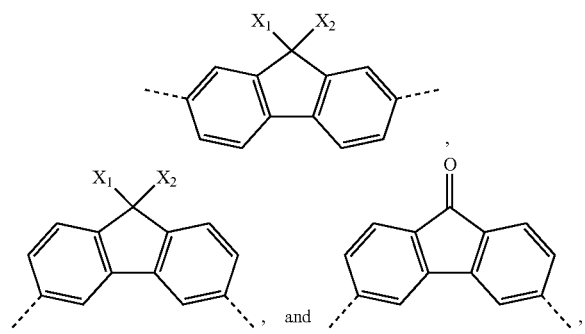

the $R_3$ is a pyridine group, a structural formula of the $R_3$ comprises one of

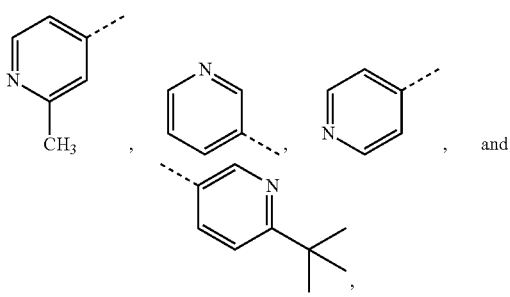

the $X_1$ comprises one of H, alkyl, alkoxy, and heteroalkyl, the $X_2$ comprises one of H, alkyl, alkoxy, and heteroalkyl.

The benefit is: the present disclosure provides an electroluminescent material, a method for manufacturing the electroluminescent material, and a luminescent device, by employing a fluorenyl group showing good planarity and strong visible π-π* absorption as π-based system, and simultaneously introducing a compound containing a carbazole group as an electron donor and a compound containing a pyridine group as an electron acceptor to realize an electroluminescent material, a method for manufacturing the electroluminescent material and a luminescent device with emitting a blue light and a high electroluminescence efficiency.

BRIEF DESCRIPTION OF DRAWINGS

In order to more clearly illustrate the technical solutions in the present application, the drawings used in the description of the embodiments will be briefly described below. It is obvious that the drawings in the following description are only some embodiments of the present application, those skilled in the art can also obtain other drawings based on these drawings without paying creative labor.

DETAILED DESCRIPTION OF PREFERRED EMBODIMENTS

Figure 1:
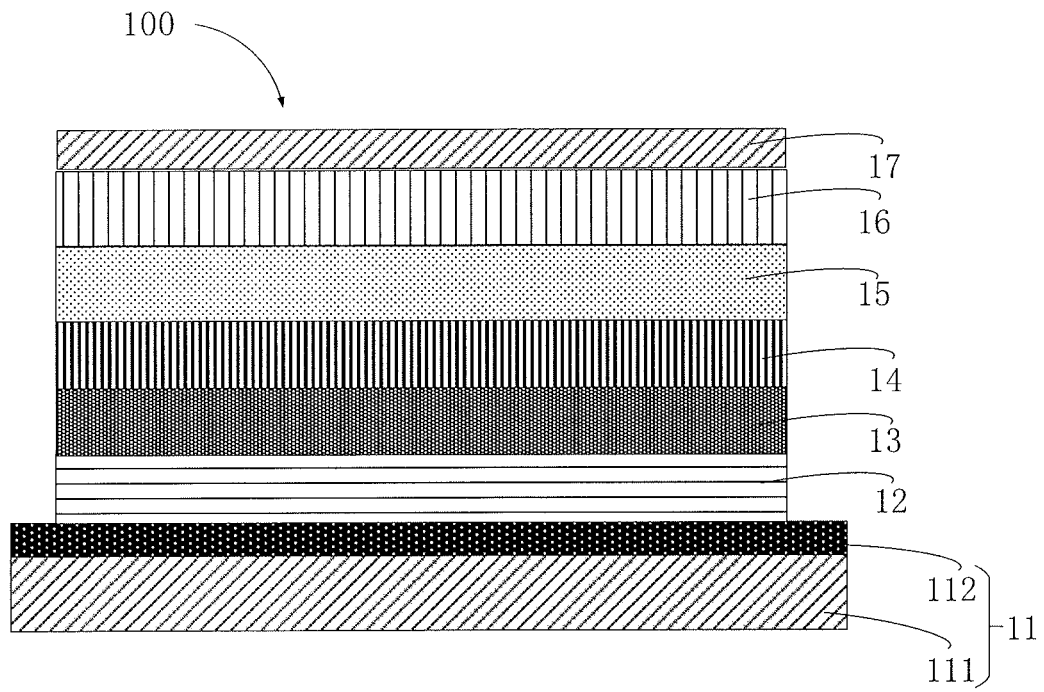
FIG. 1 is a schematic structural view of a luminescent device of the present disclosure.
Figure 2:
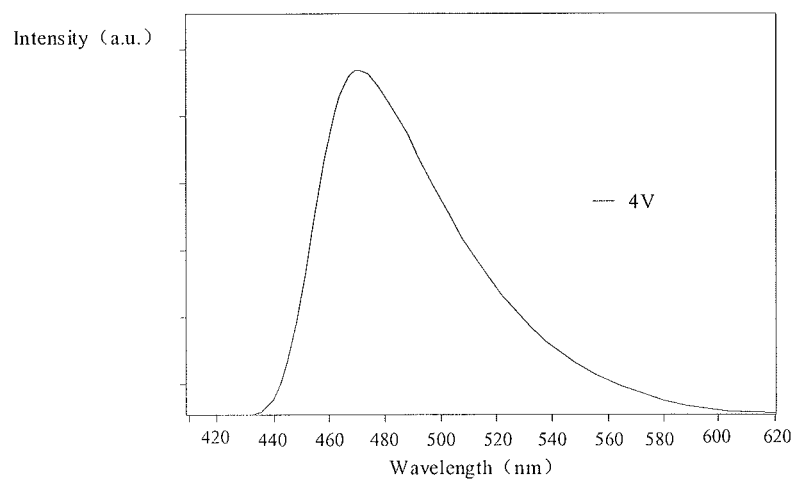
FIG. 2 is an electroluminescence spectrum of a luminescent device of the present disclosure at a driving voltage of 4V.
Figure 3:
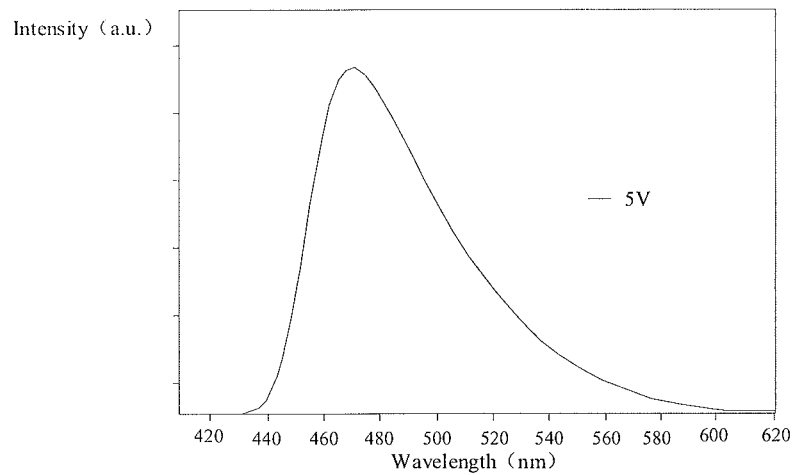
FIG. 3 is an electroluminescence spectrum of a luminescent device of the present disclosure at a driving voltage of 5V.
Figure 4:
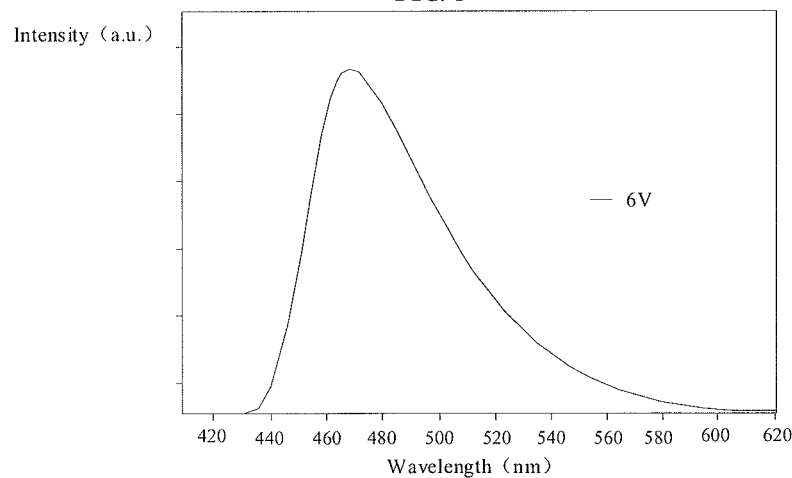
FIG. 4 is an electroluminescence spectrum of a luminescent device of the present disclosure at a driving voltage of 6V.
Figure 5:
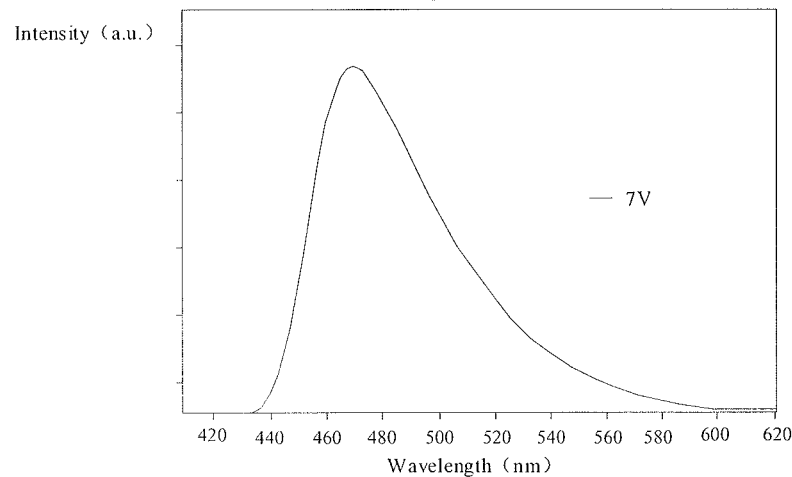
FIG. 5 is an electroluminescence spectrum of a luminescent device of the present disclosure at a driving voltage of 7V.
Figure 6:
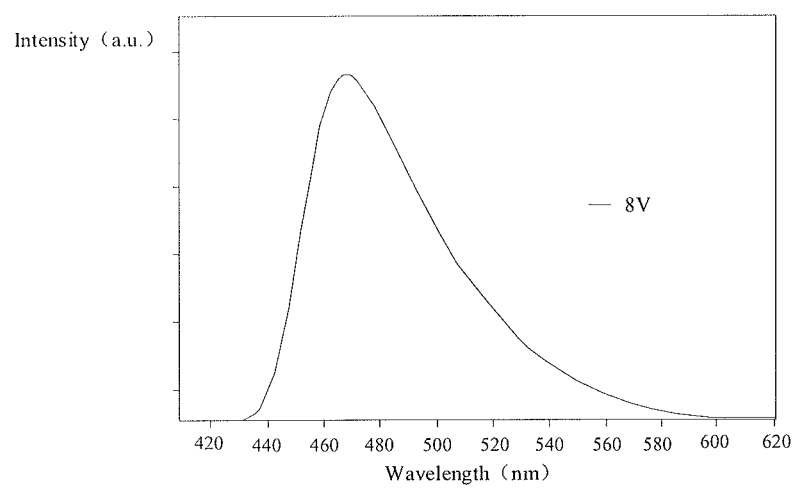
FIG. 6 is an electroluminescence spectrum of a luminescent device of the present disclosure at a driving voltage of 8V.

The present disclosure provides an electroluminescent material. A structural formula of the electroluminescent material is $R_3$—$R_2$—$R_1$—$R_2$—$R_3$, wherein the $R_1$ is a carbazole group, a structural formula of the $R_1$ includes one of

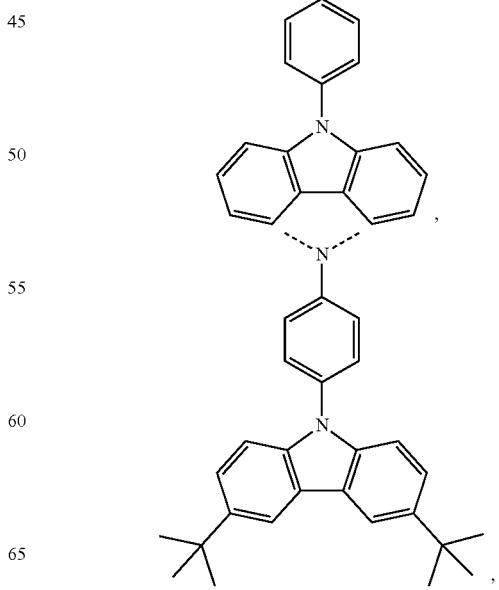

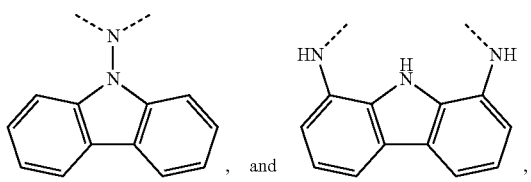, and the R$_2$ is a fluorene group, a structural formula of the R$_2$ includes one of

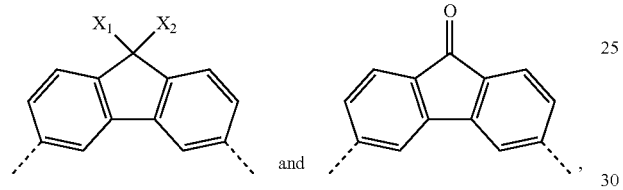, and the R$_3$ is a pyridine group, a structural formula of the R$_3$ comprises one of

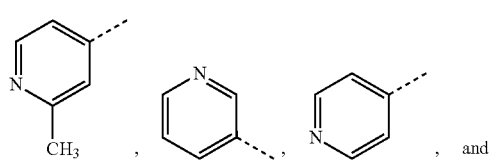, and

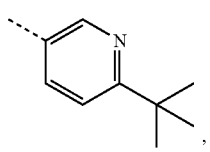, the X$_1$ comprises one of H, alkyl, alkoxy, and heteroalkyl, the X$_2$ comprises one of H, alkyl, alkoxy, and heteroalkyl. The electroluminescent material is a luminescent material emitting mazarine blue light.

The present disclosure further provides a method for manufacturing the electroluminescent material. The method for manufacturing the electroluminescent material includes:

A, providing a first reactant and a second reactant, and reacting the first reactant and the second reactant to generate a first intermediate product, wherein the first reactant comprises a compound containing a carbazole group R$_1$, the second reactant comprises a compound containing a fluorene group R$_2$, wherein a structural formula of the R$_1$ comprises one of

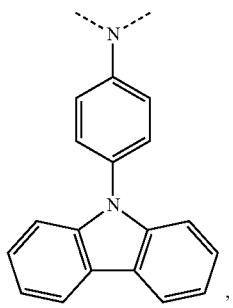

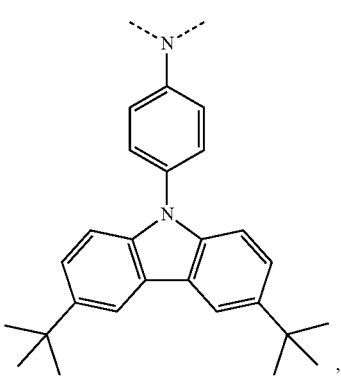, and a structural formula of the R$_2$ comprises one of

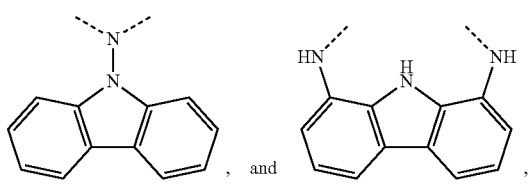, and the X$_1$ comprises one of H, alkyl, alkoxy, and heteroalkyl, the X$_2$ comprises one of H, alkyl, alkoxy, and heteroalkyl.

The first reactant includes a compound containing a carbazole group R$_1$. A structural formula of the first reactant includes one of

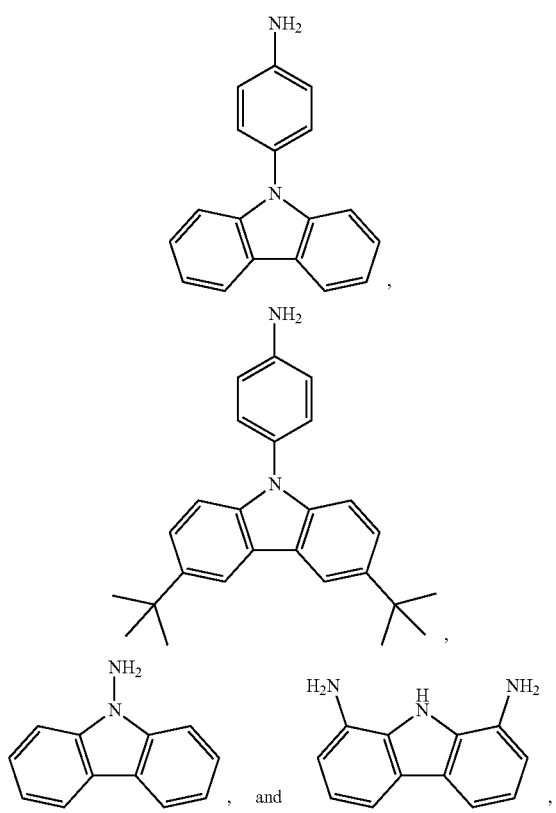

etc.

The second reactant includes a compound containing a fluorene group $R_2$. A structural formula of the second reactant includes one of

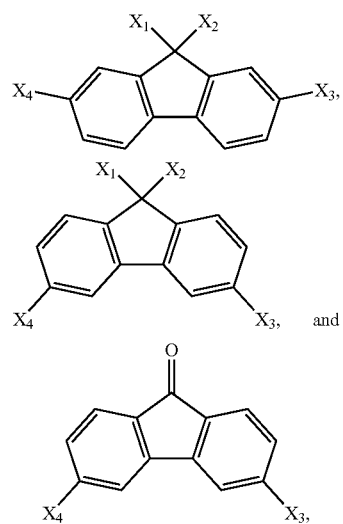

etc., wherein the $X_3$ includes one of F, Cl, Br and I, the $X_4$ includes one of F, Cl, Br and I.

The first reactant can be defined as H—$R_1$—H, and the second reactant can be defined as $X_3$—$R_2$—$X_4$, wherein a stability of the $X_3$—R bond is greater than or equal to a stability of the $X_4$—R bond.

A reaction formula of reacting the first reactant and the second reactant to generate a first intermediate product is:

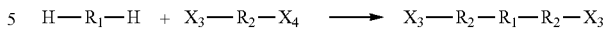

The first intermediate product can be defined as $X_3$—$R_2$—$R_1$—$R_2$—$X_3$

In the step of reacting the first reactant and the second reactant to generate a first intermediate product, a relationship between a molar weight of the first reactant and a molar weight of the second reactant is that for 1 millimole-6 millimoles of the first reactant, there are 4 millimoles-30 millimoles of the second reactant. For example, a relationship between a molar weight of the first reactant and a molar weight of the second reactant is that for 1 millimole of the first reactant, there are 4 millimoles of the second reactant. A relationship between a molar weight of the first reactant and a molar weight of the second reactant is that for 3 moles of the first reactant, there are 10 moles of the second reactant.

The first reactant and the second reactant are reacted in a first solvent to generate the first intermediate product, and the first solvent includes one or more of toluene, tetrahydrofuran, ethanol, ethylene, perchloroethylene, trichloroethylene, acetone, ethylene glycol ether, and triethanolamine.

The first solvent includes a first additive, the first additive includes one or more of sodium propan-2-olate, 1,1'-bis(diphenylphosphino)ferrocene, palladium acetate, palladium chloride, [1,1'-bis(diphenylphosphino)ferrocene]palladium dichloride, tetra-triphenyl palladium, bistriphenylphosphine palladium dichloride, tris(dibenzylideneacetone)dipalladium, allyl palladium chloride (II) dimer, potassium carbonate, cesium carbonate, potassium hydroxide, sodium hydroxide, sodium t-butoxide, and sodium bicarbonate.

In one embodiment, the first reactant can be

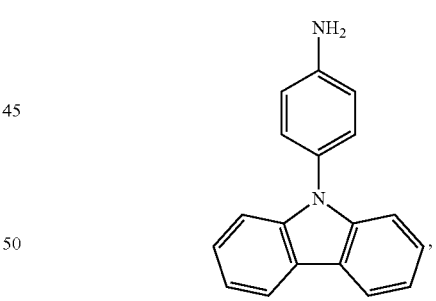

the second reactant can be

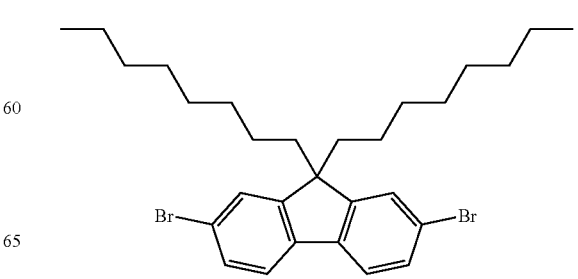

In one embodiment, a reaction formula of reacting the first reactant and the second reactant to generate the first intermediate is:

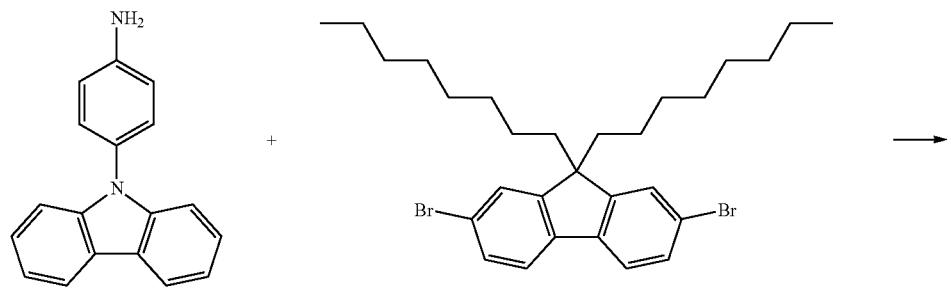

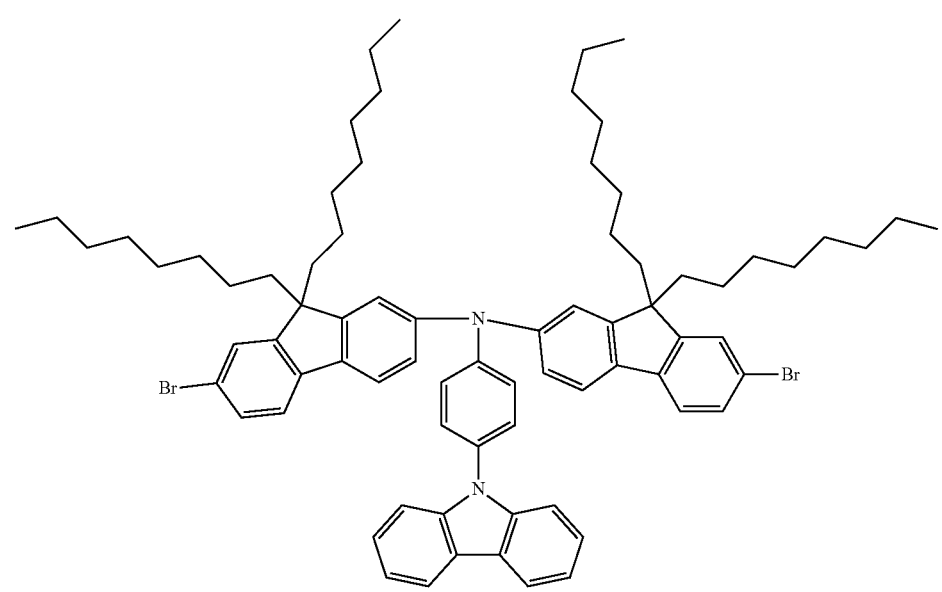

In one embodiment, 1 millimole-6 millimoles of the first reactant

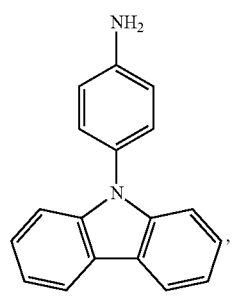 [SMILES: Nc1ccc(-n2c3ccccc3c3ccccc32)cc1]

4 millimoles-30 millimoles of the second reactant

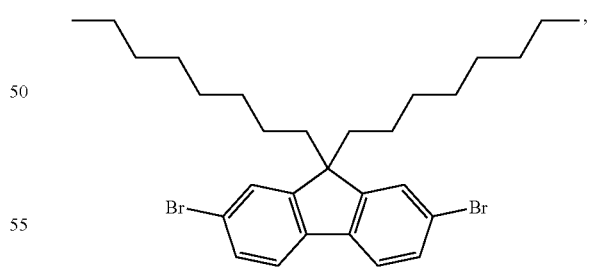

and 1 milliliter-30 milliliters of toluene and 1 millimole-13 millimoles of sodium propan-2-olate are added to a container, 0.1 millimole-5 millimoles of the 1,1'-bis(diphenylphosphino)ferrocene and 0.01 millimole-0.06 millimole of the palladium acetate are added to the container basing on an argon atmosphere, those are reacted 9 hours-36 hours at a temperature of 90 degrees Celsius-120 degrees Celsius to obtain a mixture containing the first intermediate product, and the first intermediate product

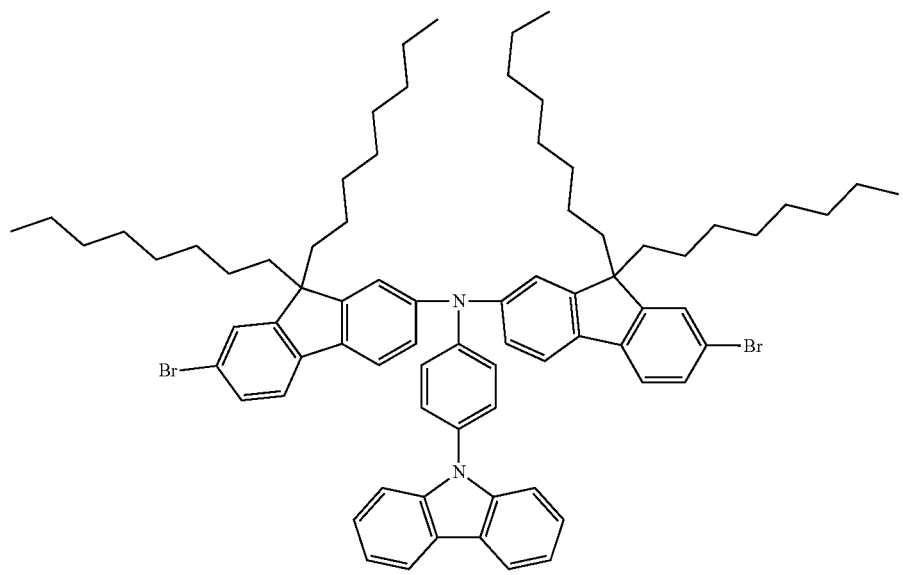 [SMILES: CCCCCCCCC1(CCCCCCCC)c2cc(Br)ccc2-c2ccc(N(c3ccc(-n4c5ccccc5c5ccccc54)cc3)c3ccc4c(c3)C(CCCCCCCC)(CCCCCCCC)c3cc(Br)ccc3-4)cc21]

is obtained by a separating and purifying process.

B, providing a third reactant, and reacting the first intermediate product and the third reactant to generate the electroluminescent material, wherein a structural formula of the electroluminescent material is $R_3—R_2—R_1—R_2—R_3$, the third reactant comprises a compound containing a pyridine group $R_3$, a structural formula of the $R_3$ comprises one of

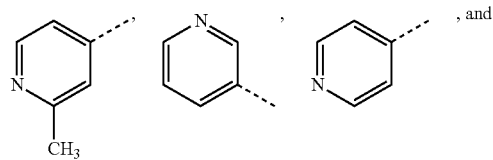, and

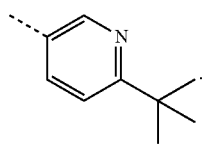

The third reactant comprises a compound containing a pyridine group $R_3$. A structural formula of the third reactant can be one of

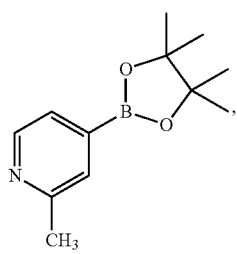

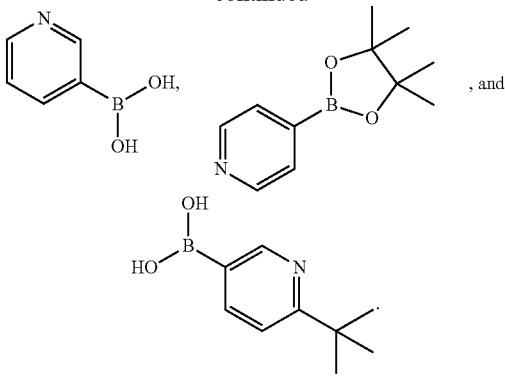

The first intermediate product can be $X_3—R_2—R_1—R_2—X_3$. The third reactant can be $R_3—Y$. The Y includes a boric acid pinacol ester group or a boric acid group.

A reaction formula of reacting the first intermediate product and the third reactant to generate the electroluminescent material is:

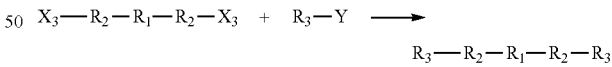

In the step of reacting the first intermediate product and the third reactant to generate the electroluminescent material, a relationship between a molar weight of the first intermediate product and a molar weight of the third reactant is that for 0.3 millimole-12 millimoles of the first intermediate product, there are 0.1 millimoles-5.9 millimoles of the third reactant. For example, a relationship between a molar weight of the first intermediate product and a molar weight of the third reactant is that for 1 millimole of the first intermediate product, there is 1 millimole of the third reactant. A relationship between a molar weight of the first intermediate product and a molar weight of the third reactant is that for 3 moles of the first intermediate product, there are 5 moles of the third reactant.

The first intermediate and the third reactant are reacted in a second solvent to generate the electroluminescent material, and the second solvent includes one or more of toluene, tetrahydrofuran, ethanol, ethylene, perchloroethylene, trichloroethylene, acetone, ethylene glycol ether, and triethanolamine.

The second solvent includes a second additive, the second additive includes one or more of tetra-triphenyl palladium, sodium propan-2-olate, 1,1'-bis(diphenylphosphino)ferrocene, palladium acetate, palladium chloride, [1,1'-bis(diphenylphosphino)ferrocene]palladium dichloride, bistriphenylphosphine palladium dichloride, tris(dibenzylideneacetone)dipalladium, ally palladium chloride (II) dimer, potassium carbonate, cesium carbonate, potassium hydroxide, sodium hydroxide, sodium t-butoxide, and sodium bicarbonate.

The structural formula of the electroluminescent material is $R_3$—$R_2$—$R_1$—$R_2$—$R_3$, wherein a structural formula of the $R_1$ includes one of

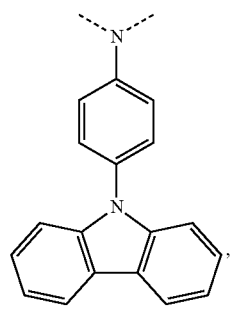

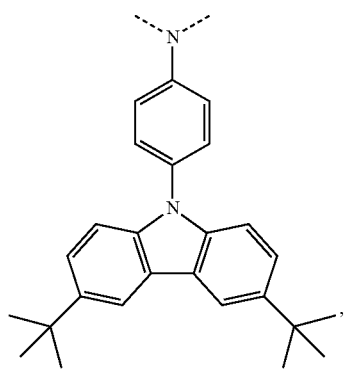

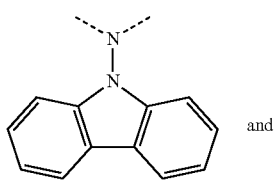 and

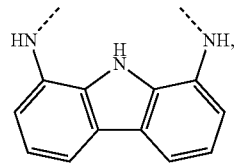

a structural formula of the $R_2$ includes one of

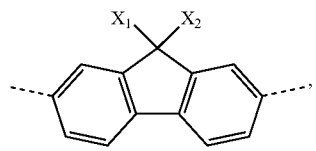

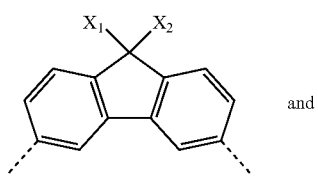 and

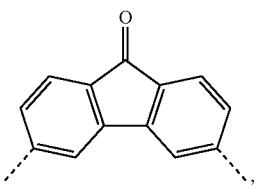

a structural formula of the R3 is

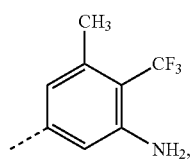

the $X_1$ includes one of H, alkyl, alkoxy and heteroalkyl, the $X_2$ includes one of H, alkyl, alkoxy and heteroalkyl, a structural formula of the $R_3$ comprises one of

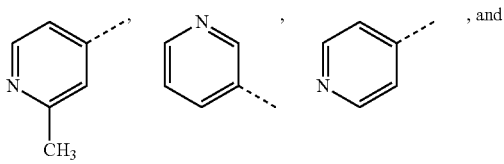

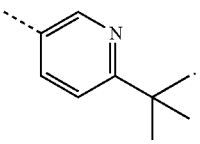

In one embodiment, the first intermediate product can be
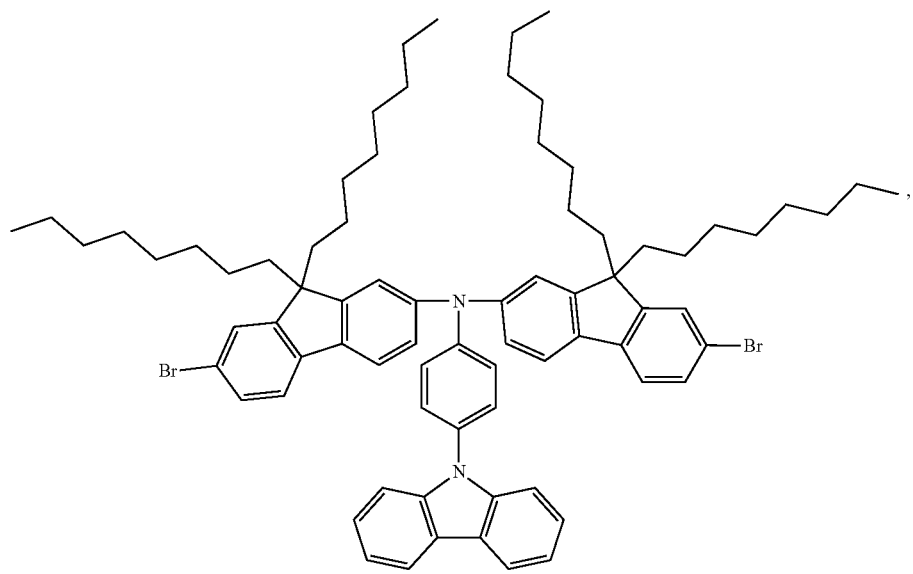 [SMILES: CCCCCCCCC1(CCCCCCCC)c2cc(Br)ccc2-c2ccc(N(c3ccc(-n4c5ccccc5c5ccccc54)cc3)c3ccc4c(c3)C(CCCCCCCC)(CCCCCCCC)c3cc(Br)ccc3-4)cc21]
the third reactant can be
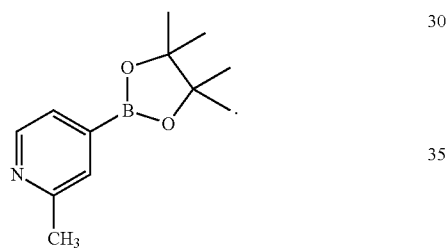
A reaction formula of reacting the first intermediate product and the third reactant to generate the electroluminescent material is:
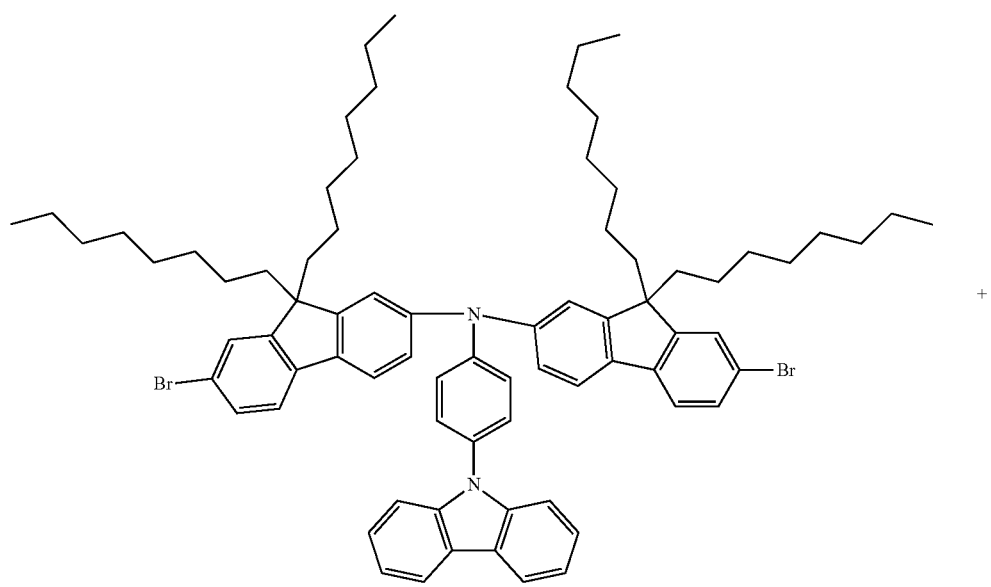

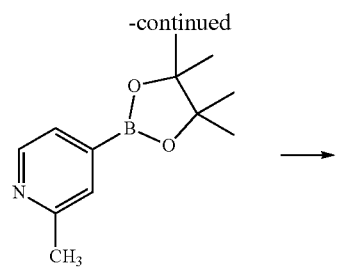
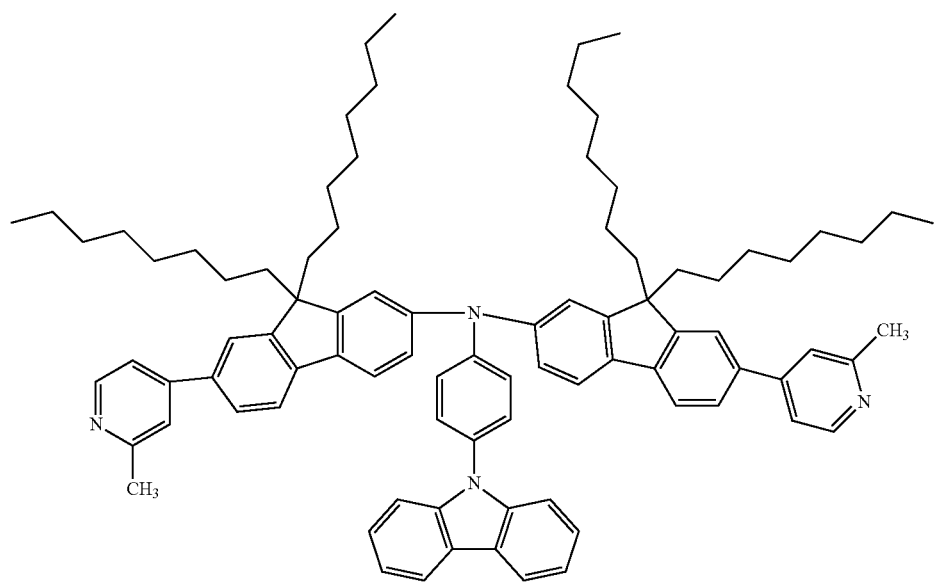
40
In one embodiment, 0.3 millimoles-12 millimoles of the first intermediate product
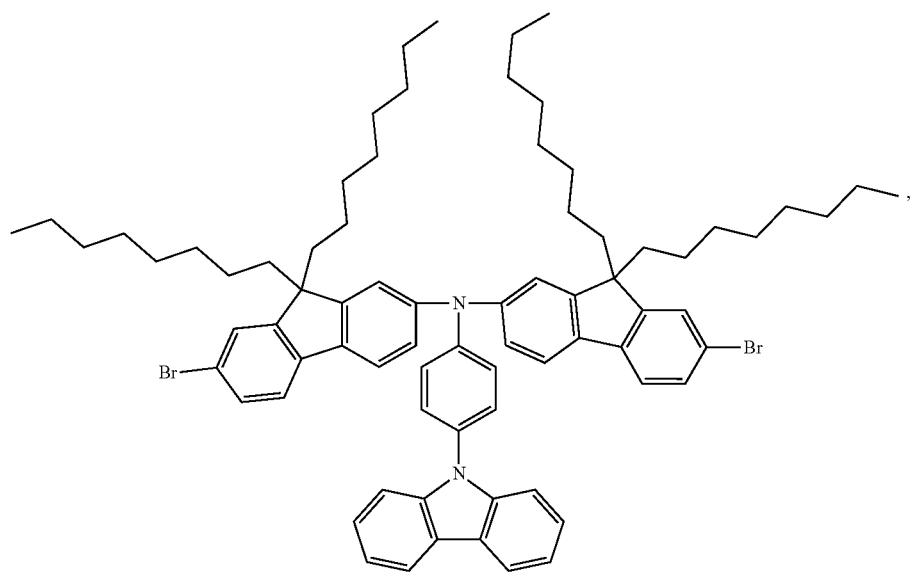 [SMILES: CCCCCCCCC1(CCCCCCCC)c2cc(Br)ccc2-c2ccc(N(c3ccc(-n4c5ccccc5c5ccccc54)cc3)c3ccc4c(c3)C(CCCCCCCC)(CCCCCCCC)c3cc(Br)ccc3-4)cc21]

0.1 millimoles-5.9 millimoles of the third reactant

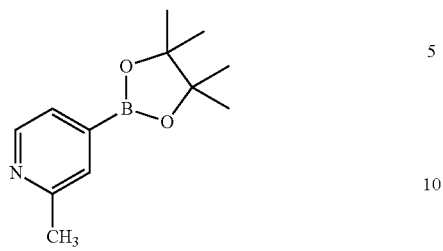

are added in a container, an appropriate amount of toluene and a potassium carbonate solution are added, 0.001 millimoles-0.99 millimoles of tetrakistriphenylphosphorus palladium are added by dividing into two portions basing on an argon atmosphere, those are reacted 9 hours-36 hours at a temperature of 90 degrees Celsius-120 degrees Celsius to obtain a mixture containing the first electroluminescent material, the electroluminescent material

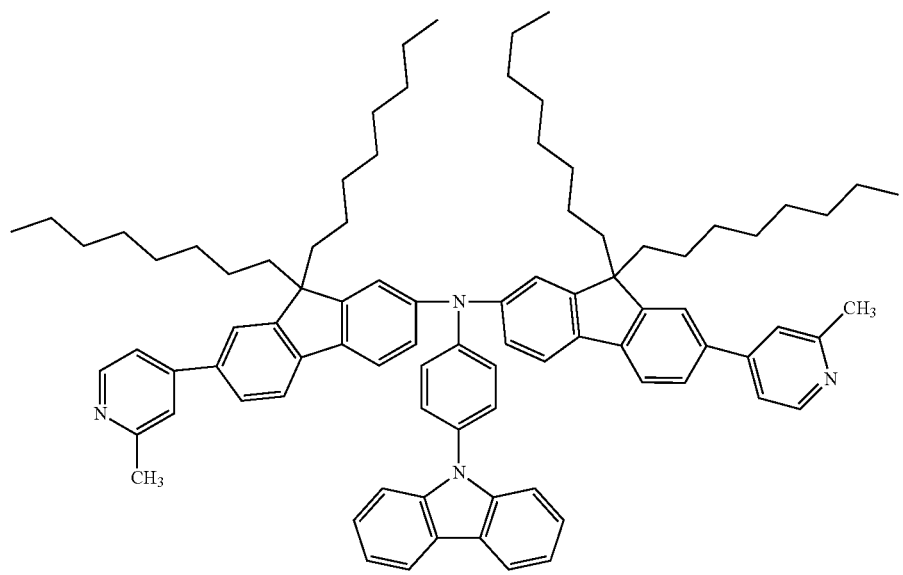 [SMILES: CCCCCCCCC1(CCCCCCCC)c2cc(-c3ccnc(C)c3)ccc2-c2ccc(N(c3ccc(-n4c5ccccc5c5ccccc54)cc3)c3ccc4c(c3)C(CCCCCCCC)(CCCCCCCC)c3cc(-c5ccnc(C)c5)ccc3-4)cc21]

are obtained by a separating and purifying process.

In separating and purifying process, first, the mixture cool down to a room temperature, then the reaction solution is poured into an ice water and extracted twice to five times by an extraction solvent to obtain the organic phase, to be dried by $Na_2SO_4$ and to suspend and evaporate the water, and a chromatography process is employed by a chromatographic column to obtain a solid powder which is the electroluminescent material.

The extraction solvent includes one or more of ether, dichloromethane, chloroform, and tetrahydrofuran. A ratio of the chromatographic column is a volume of dichloromethane to a volume of n-hexane ranging from 1:0.5 to 1:10.

Referring to FIG. 1, the present disclosure providing a luminescent device 100. The luminescent device 100 includes a substrate layer 11, a hole injection layer 12, a hole transport layer 13, a luminescent layer 14, an electronic transport layer 15, an electronic injection layer 16, and a cathode layer 17.

The substrate layer 11 includes a base 111 and an anode layer 112. The base 111 can be a glass base or a transparent plastic base. The anode layer 112 is formed on the base 111.

The anode layer 112 can be made of indium tin oxide. The hole injection layer 12 is formed on the anode layer 112. The hole transport layer 13 is formed on the hole injection layer 12. The luminescent layer 14 is formed on the hole transport layer 13. The luminescent layer 14 includes the electroluminescent material. A structural formula of the electroluminescent material is $R_3$—$R_2$—$R_1$—$R_2$—$R_3$, wherein $R_1$ is a carbazole group, a structural formula of the $R_1$ includes one of

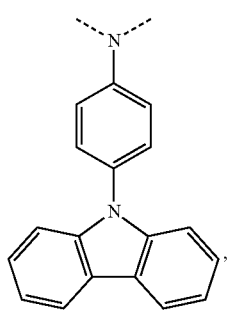

-continued

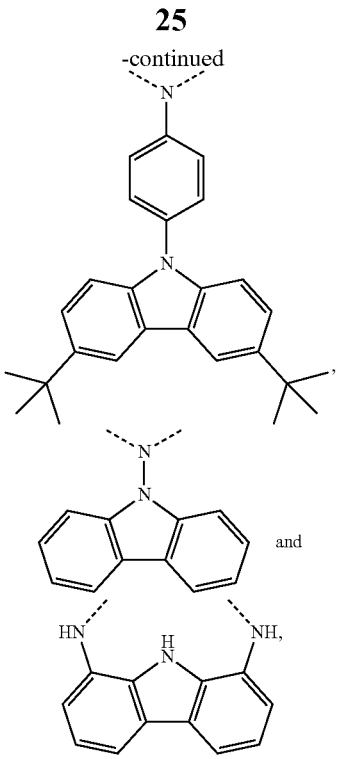

and the $R_2$ is a fluorene group, a structural formula of the $R_2$ includes one of

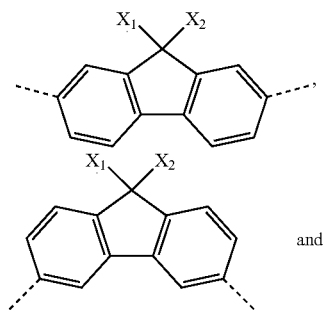

and

-continued

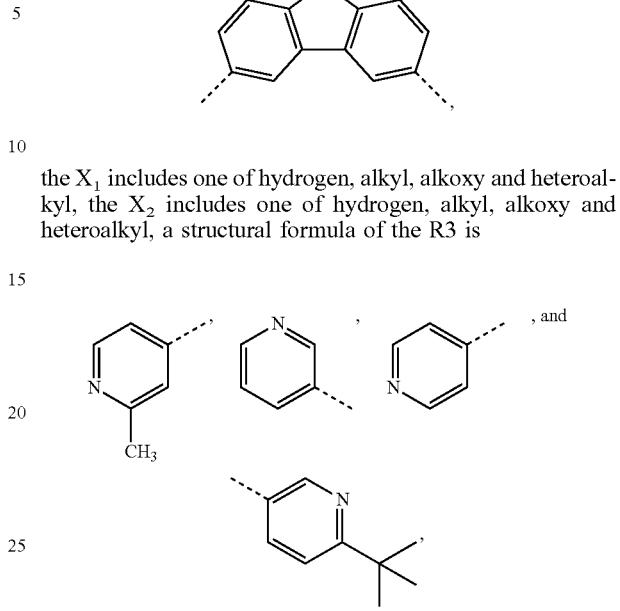

the $X_1$ includes one of hydrogen, alkyl, alkoxy and heteroalkyl, the $X_2$ includes one of hydrogen, alkyl, alkoxy and heteroalkyl, a structural formula of the R3 is , and The electronic transport layer 15 is formed on the luminescent layer 14. The electronic injection layer 16 is formed on the electronic transport layer 15. The cathode 17 is formed on the electronic injection layer 16. The cathode layer 17 is made of lithium fluoride/aluminum.

Referring to FIGS. 2-6, FIGS. 2-6 are electroluminescence spectrums of the luminescent device of the present disclosure at a driving voltage of 4V, 5V, 6V, 7V and 8V. At different driving voltages, a maximum emission peak position of the electroluminescent material of the luminescent layer 14 is located at around 456 nm-480 nm. The electroluminescent material is a luminescent material emitting mazarine blue light. A fluorescence quantum yield of the electroluminescent material

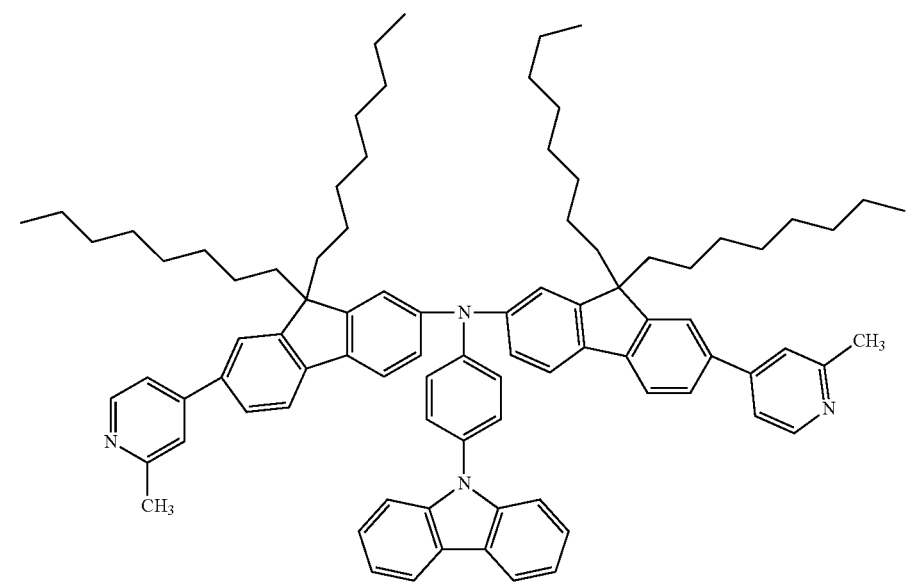 [SMILES: CCCCCCCCC1(CCCCCCCC)c2cc(-c3ccnc(C)c3)ccc2-c2ccc(N(c3ccc(-n4c5ccccc5c5ccccc54)cc3)c3ccc4c(c3)C(CCCCCCCC)(CCCCCCCC)c3cc(-c5ccnc(C)c5)ccc3-4)cc21]

measuring by a steady state/transient fluorescence spectrometer is 96.5%.

The present disclosure provides an electroluminescent material, a method for manufacturing the electroluminescent material, and a luminescent device, by employing a fluorenyl group showing good planarity and strong visible π-π* absorption as π-based system, and simultaneously introducing a compound containing a carbazole group as an electron donor and a compound containing a pyridine group as an electron acceptor to realize an electroluminescent material, a method for manufacturing the electroluminescent material and a luminescent device with emitting a blue light and a high electroluminescence efficiency.

The embodiments of the present application are described in detail above, and the principles and implementations of the present application are set forth in the specific examples. The description of the above embodiments is only for helping to understand the present application. In the meantime, those skilled in the art will be able to change the specific embodiments and the scope of the application according to the idea of the present application. In the above, the content of the specification should not be construed as limiting the present application.

What is claimed is:

1. A method for manufacturing an electroluminescent material, comprising:
providing a first reactant and a second reactant, and reacting the first reactant and the second reactant to generate a first intermediate product, wherein the first reactant comprises a compound containing a carbazole group $R_1$, the second reactant comprises a compound containing a fluorene group $R_2$, wherein a structural formula of the $R_1$ comprises one of

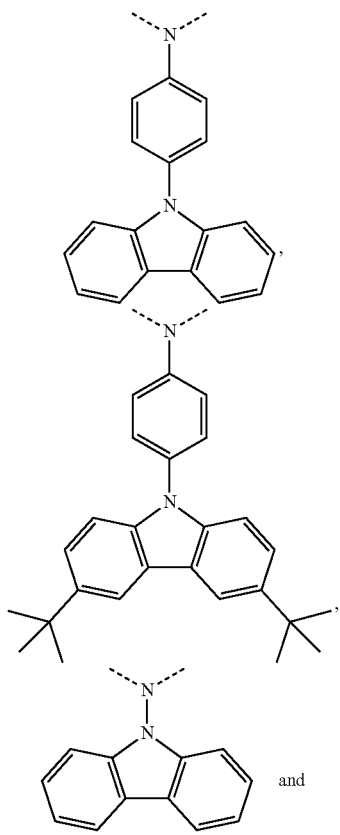

and

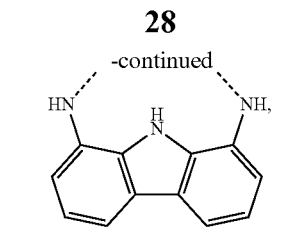

a structural formula of the $R_2$ comprises one of

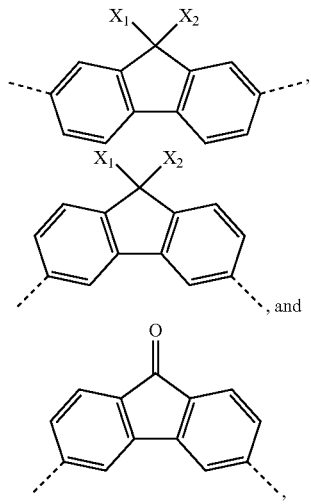

the $X_1$ comprises one of H, alkyl, alkoxy, and heteroalkyl, the $X_2$ comprises one of H, alkyl, alkoxy, and heteroalkyl; and providing a third reactant, and reacting the first intermediate product and the third reactant to generate the electroluminescent material, wherein a structural formula of the electroluminescent material is $R_3$—$R_2$—$R_1$—$R_2$—$R_3$, the third reactant comprises a compound containing a pyridine group $R_3$, a structural formula of the $R_3$ comprises one of

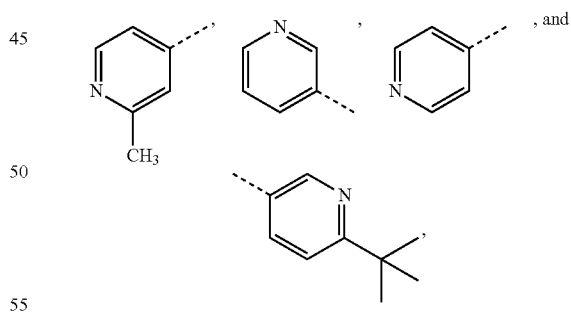

wherein the third reactant is $R_3$—Y, the Y comprises a boric acid pinacol ester group or a boric acid group.

2. The method for manufacturing the electroluminescent material of claim 1, wherein in the step of reacting the first reactant and the second reactant to generate a first intermediate product, a relationship between a molar weight of the first reactant and a molar weight of the second reactant is that for 1 millimole-6 millimoles of the first reactant, there are 4 millimoles-30 millimoles of the second reactant.

3. The method for manufacturing the electroluminescent material of claim 1, wherein the first reactant and the second reactant are reacted in a first solvent to generate the first intermediate product, the first solvent comprises one or more of toluene, tetrahydrofuran, ethanol, ethylene, perchloroethylene, trichloroethylene, acetone, ethylene glycol ether, and triethanolamine.

4. The method for manufacturing the electroluminescent material of claim 3, wherein the first solvent comprises a first additive, the first additive comprises one or more of sodium propan-2-olate, 1,1'-bis(diphenylphosphino)ferrocene, palladium acetate, palladium chloride, [1,1'-bis(diphenylphosphino)ferrocene]palladium dichloride, tetra-triphenyl palladium, bistriphenylphosphine palladium dichloride, tris(dibenzylideneacetone)dipalladium, allyl palladium chloride (II) dimer, potassium carbonate, cesium carbonate, potassium hydroxide, sodium hydroxide, sodium t-butoxide, and sodium bicarbonate.

5. The method for manufacturing the electroluminescent material of claim 4, wherein the first solvent comprises toluene, the first additive comprises sodium propan-2-olate, 1,1'-bis(diphenylphosphino)ferrocene, and palladium acetate.

6. The method for manufacturing the electroluminescent material of claim 5, wherein a relationship among a molar weight of sodium propan-2-olate, a molar weight of 1,1'-bis(diphenylphosphino)ferrocene and a molar weight of palladium acetate in the first additive is that for 1 millimole-13 millimoles of sodium propan-2-olate, there are 0.1 millimoles-5 millimoles of 1,1'-bis(diphenylphosphino)ferrocene and 0.01 millimole-0.06 millimole of palladium acetate.

7. The method for manufacturing the electroluminescent material of claim 1, wherein in the step of reacting the first intermediate product and the third reactant to generate the electroluminescent material, a relationship between a molar weight of the first intermediate product and a molar weight of the third reactant is that for 0.3 millimoles-12 millimoles of the first intermediate product, there are 0.1 millimoles-5.9 millimoles of the third reactant.

8. The method for manufacturing the electroluminescent material of claim 1, wherein the first intermediate product and the third reactant are reacted in a second solvent to generate the electroluminescent material, the second solvent comprises one or more of toluene, tetrahydrofuran, ethanol, ethylene, perchloroethylene, trichloroethylene, acetone, ethylene glycol ether, and triethanolamine.

9. The method for manufacturing the electroluminescent material of claim 8, wherein the second solvent comprises a second additive, the second additive comprises one or more of tetra-triphenyl palladium, sodium propan-2-olate, 1,1'-bis(diphenylphosphino)ferrocene, palladium acetate, palladium chloride, [1,1'-bis(diphenylphosphino)ferrocene]palladium dichloride, bistriphenylphosphine pallride, tris(dibenzylideneacetone)dipalladium, allyl palladium chloride (II) dimer, potassium carbonate, cesium carbonate, potassium hydroxide, sodium hydroxide, sodium t-butoxide, and sodium hydrogencarbonate.

10. The method for manufacturing the electroluminescent material of claim 8, wherein the second solvent comprises toluene, the second additive comprises potassium carbonate aqueous solution, and tetra-triphenyl palladium.

11. The method for manufacturing the electroluminescent material of claim 1, wherein in the step of providing a first reactant and a second reactant, and reacting the first reactant and the second reactant to generate a first intermediate product, wherein a reaction temperature is 90 degrees Celsius-120 degrees Celsius.

12. The method for manufacturing the electroluminescent material of claim 11, wherein in the step of providing a first reactant and a second reactant, and reacting the first reactant and the second reactant to generate a first intermediate product, wherein a reaction time is 9 hours-36 hours.

13. The method for manufacturing the electroluminescent material of claim 1, wherein in the step of providing a third reactant, and reacting the first intermediate product and the third reactant to generate the electroluminescent material, wherein a reaction temperature is 90 degree Celsius-120 degree Celsius.

14. The method for manufacturing the electroluminescent material of claim 13, wherein in the step of providing a third reactant, and reacting the first intermediate product and the third reactant to generate the electroluminescent material, wherein a reaction time is 9 hours to 36 hours.

15. The method for manufacturing the electroluminescent material of claim 1, wherein a structural formula of the first reactant comprises one of

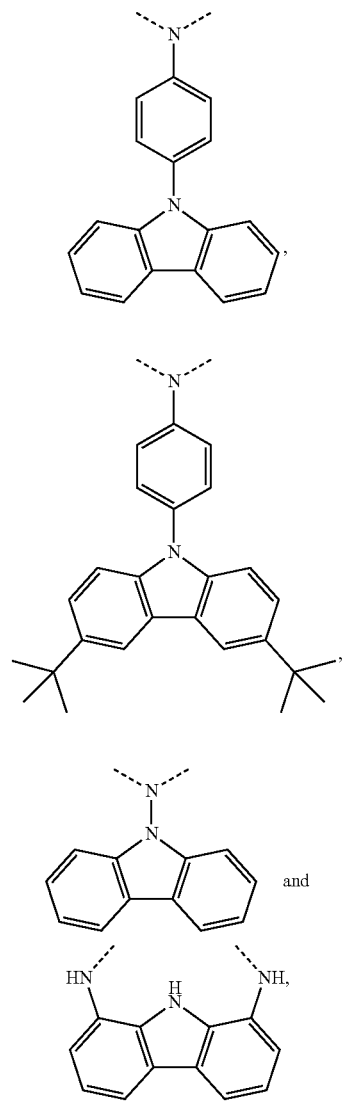

16. The method for manufacturing the electroluminescent material of claim 1, wherein a structural formula of the second reactant comprises one of

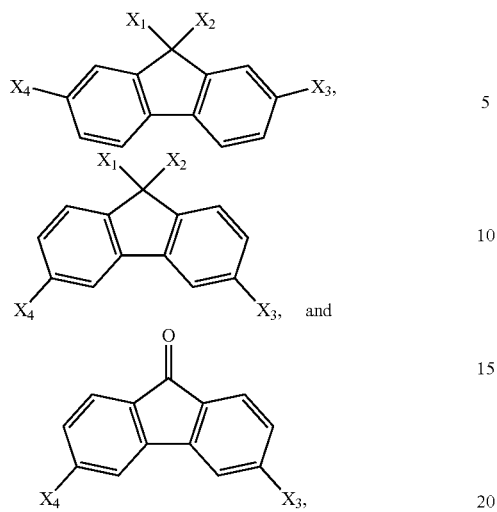
wherein the $X_3$ includes one of F, Cl, Br, and I, the $X_4$ includes one of F, Cl, Br, and I.
* * * * *